United States Patent
Oleniczak et al.

(10) Patent No.: US 10,960,108 B2
(45) Date of Patent: Mar. 30, 2021

(54) DECELLULARIZED AND DEMINERALIZED BONE MATRICES AND METHODS FOR MAKING SAME

(71) Applicant: FABRICO TECHNOLOGY INC, Georgetown, TX (US)

(72) Inventors: Joseph Oleniczak, Austin, TX (US); Robert Chin, Austin, TX (US)

(73) Assignee: FABRICO TECHNOLOGY INC, Georgetown, TX (US)

(*) Notice: Subject to any disclaimer, the term of this patent is extended or adjusted under 35 U.S.C. 154(b) by 157 days.

(21) Appl. No.: 16/008,769

(22) Filed: Jun. 14, 2018

(65) Prior Publication Data
US 2018/0361024 A1    Dec. 20, 2018

Related U.S. Application Data

(60) Provisional application No. 62/519,277, filed on Jun. 14, 2017.

(51) Int. Cl.
- A61L 27/38 (2006.01)
- A61L 27/36 (2006.01)
- A61L 27/22 (2006.01)

(52) U.S. Cl.
CPC ......... *A61L 27/3608* (2013.01); *A61L 27/365* (2013.01); *A61L 27/3683* (2013.01); *A61L 27/3691* (2013.01); *A61L 27/3821* (2013.01); *A61L 27/3834* (2013.01); *A61L 27/227* (2013.01); *A61L 2300/414* (2013.01); *A61L 2300/426* (2013.01); *A61L 2430/40* (2013.01); *C12Y 304/21062* (2013.01)

(58) Field of Classification Search
CPC .................................................. A61L 27/3608
See application file for complete search history.

(56) References Cited

U.S. PATENT DOCUMENTS

| | | | |
|---|---|---|---|
| 4,810,691 A * | 3/1989 | Seyedin | A61K 35/32 514/16.7 |
| 2014/0255506 A1* | 9/2014 | Behnam | A61L 27/3608 424/549 |
| 2014/0302481 A1* | 10/2014 | Chin | A61L 27/3691 435/1.2 |

FOREIGN PATENT DOCUMENTS

CN      105435307 A   *   3/2016

* cited by examiner

*Primary Examiner* — Michael F Pepitone (57) ABSTRACT

A method of making a bone matrix includes exposing a bone tissue to a solution including a surfactant and a protease; treating the bone tissue with an acid solution following exposing the bone tissue; and electrophoretically treating the acid treated bone tissue. A bone matrix has a DNA content of not greater than 0.1 micrograms per milligram sample and a modulus in a range of 180 kPa to 250 kPa.

20 Claims, 8 Drawing Sheets

DECELLULARIZED AND DEMINERALIZED BONE MATRICES AND METHODS FOR MAKING SAME

CROSS-REFERENCE TO RELATED APPLICATION(S)

This application claims benefit of U.S. Provisional Application No. 62/519,277, filed Jun. 14, 2017, which is incorporated herein by reference in its entirety.

FIELD OF THE DISCLOSURE

This disclosure in general relates to methods for forming decellularized and demineralized bone matrices and to decellularized and demineralized bone matrices made through such methods.

BACKGROUND

A considerable number of traumatic events, surgeries, and degenerative conditions result in damage to the skeletal system. For example, car accidents or sports injuries often result in shattered bone. Similarly, surgeries, such as cranial surgery, can involve the resection of bone, such as the cranium. Further, arthritic conditions or cancers can result in degenerated vertebrae.

As such, the medical field is seeking improved methods and devices to treat skeletal injuries.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an example embodiment, a decellularized and demineralized bone matrix, generally referred to herein as demineralized bone matrix (DBM), has a DNA content of not greater than 0.1 ng/milligram and a Young's modulus in a range of 180 kPa to 250 kPa. Such a DBM can be implanted, for example, in a volume at which bone was resected or where bone growth is desired. In an example, the DBM can be derived from a mammalian donor and implanted into a mammalian recipient either of the same species or a different species.

In a further embodiment, a demineralized bone matrix can be formed by breaking surface cellular matrices residing on a bone matrix, demineralizing the remaining bone matrix, and further removing undesired biomarkers, such as polynucleotides from the demineralized bone matrix. In an example, a bone matrix is exposed to a solution including a protease enzyme and optionally a surfactant. For example, the protease enzyme can be a subtilisin enzyme. In a further example, the bone matrix can be demineralized in an acid solution, such as a hydrochloric acid solution. Following demineralization, the bone matrix can be further treated using an electrophoretic apparatus. For example, the bone matrix solution can be placed in a surfactant solution or gel and exposed to a potential difference in the electrophoretic apparatus. In addition, the bone matrix can be further treated in an electrophoretic apparatus in deionized water.

Figure 1:
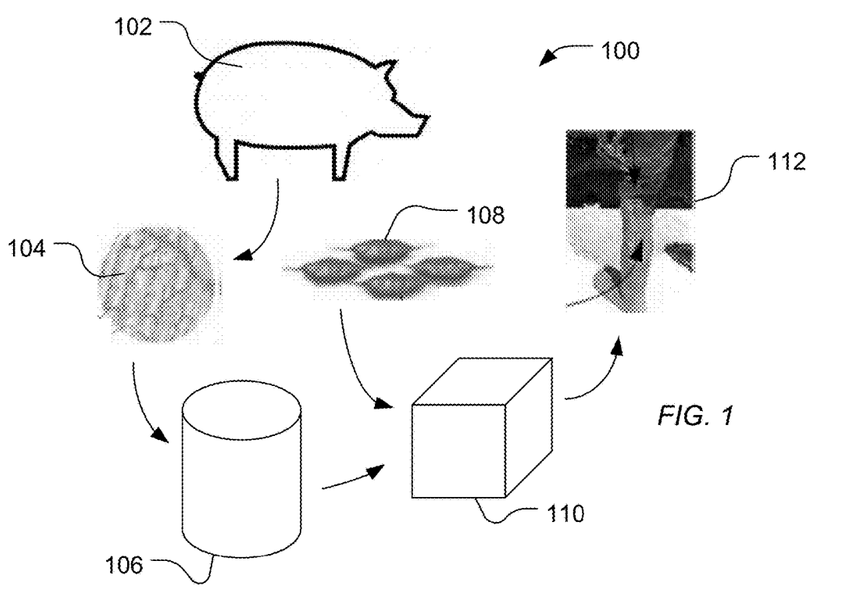
FIG. 1 includes an illustration of an example process for forming a demineralized bone matrix.

As illustrated in the process 100 of FIG. 1, a tissue 104, such as a bone matrix, is derived from a donor 102. In an example, the donor 102 is a mammalian donor. For example, the donor can be an allogeneic or a xenogeneic donor. In an example, the donor 102 is a patient. The tissue sample 104 can be a bone matrix and optionally can include other tissues such as muscle tissue, vascular tissue, organ tissue, ligaments, tendons, nerve tissue, brain tissue, cartilage, ureter tissue, bladder tissue, or any combination thereof. The tissue sample 104 can be a cranial bone, vertebral bone, femoral bone, humeral bone, phalangeal bone, or any combination thereof.

The tissue sample 104 can be pretreated, exposing the tissue 104 to a hypotonic or hypertonic solution, a surfactant solution, buffers, protease inhibitors, enzymatic treatment, a wash solution, or any combination thereof.

The tissue sample 104 is treated in an electrophoretic apparatus 106. Such an electrophoretic apparatus 106 removes cellular material from the tissue sample 104, leaving a demineralized bone matrix (DBM). The electrophoretic apparatus 106 includes a container, at least two electrodes, and a tissue support. A composition is placed along with the tissue sample in the electrophoretic apparatus 106. The composition is in contact with the electrodes and the tissue sample. A voltage potential is applied across the electrodes, and cellular material is removed from the tissue sample, leaving the demineralized bone matrix (DBM). In addition, the composition can be perfused into the tissue using existing vascular structures or using needles. Following decellularization, the DBM can be washed or can be pretreated with agents to enhance growth, such as growth factors, cytokines such as chemokines, PEGylated fibrinogen, or any combination thereof.

Optionally, the demineralized bone matrix (DBM) is transferred to a regeneration device 110, along with cells 108, to repopulate the DBM in vitro. The cells 108 can be differentiated cells specific to the desired tissue type. In another example, the cells 108 are stem cells. The stems cells can be totipotent, pluripotent, multipotent, oligopotent, or unipotent stem cells, and can be derived from zygote, embryonic, or adult sources. In particular, bone marrow mesenchymal cells can be used either in vitro or in vivo to repopulate an DBM. The cells 108 repopulate the demineralized bone matrix (DBM), generating replacement tissue. The replacement tissue may be implanted in a patient 112. Alternatively, the demineralized bone matrix (DBM) can be implanted in the patient 112 without the application of cells 108.

Figure 2:
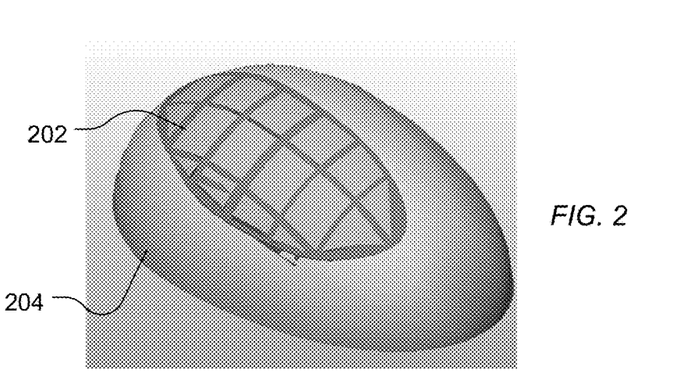
FIG. 2 and FIG. 3 include illustrations of example implants for addressing cranial resections.
Figure 3:
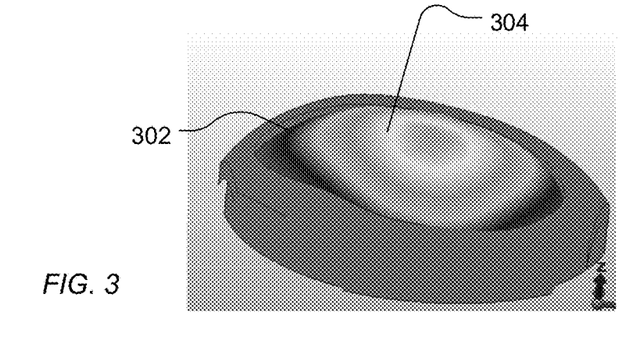

In an example, a demineralized bone matrix having a desirable low amount of polynucleotides or biological markers that instigate rejection and having a desirable flexibility or modulus can be used in addressing cranial injuries or assisting with recovery from brain surgeries. In an example, such a demineralized bone matrix (DBM) can be applied over an opening in the skull or cranium, as illustrated in FIG. 2. In an example, the demineralized bone matrix (DBM) 204 can be applied to a whole or opening in the cranium 202. Over time, the demineralized bone matrix (DBM) 202 can calcify or develop into mineralized bone through the actions of osteoclasts and osteoblasts, effectively forming new cranial material over the former opening into the cranial cavity. Advantageously, the DBM can also be flexible in the short term. For example, as illustrated in FIG. 3, the demineralized bone matrix (DBM) 302 can permit a degree of deformation, as illustrated at 304, in response to changes in pressure inside the cranial cavity. In particular, such flexibility can compensate for changes in pressure within the cranial cavity on the order of 26 mmHg Such a relief of pressure and compensation for swelling can alleviate problems associated with brain injuries in the short term, while allowing for long-term formation of a bone structure.

Figure 4:
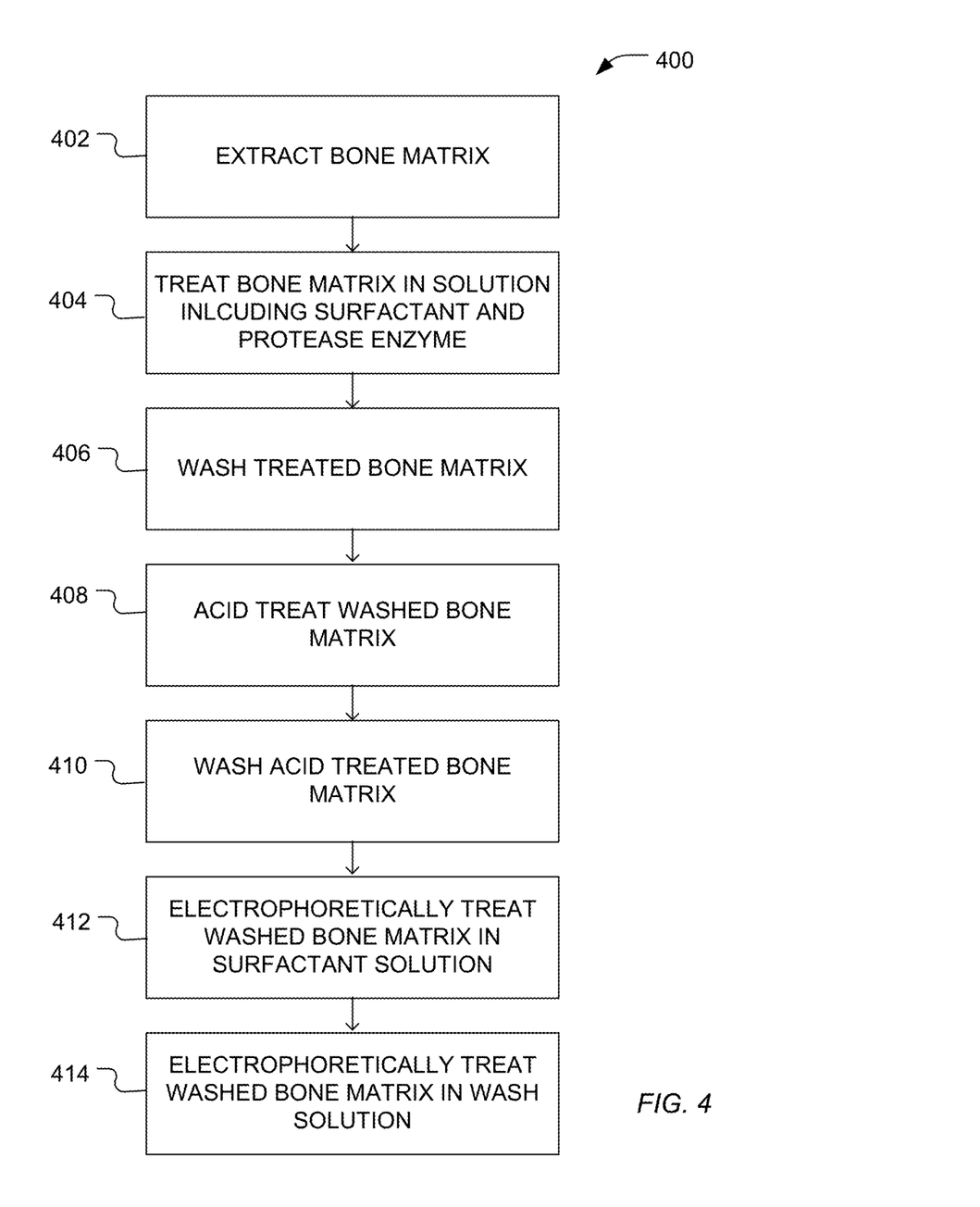
FIG. 4 includes a flow diagram illustrating an example method for forming a demineralized bone matrix.

As illustrated in FIG. 4, a method 400 for forming demineralized bone matrix (DBM) can include extracting bone matrix from a donor, as illustrated block 402. The bone matrix can be derived from a donor, such as a mammalian donor. Based on its intended use, the bone matrix can be allogeneic or xenogeneic. Optionally, the bone matrix is derived from a similar bone structure as the bone structure to which the resulting DBM is to be applied. Alternatively, the DBM can be derived from bone having a different structure than the structure being replaced by the DBM. For example, the DBM can be derived from a skull with the intent to use it to replace skull bone structures. In another example, the DBM can be derived from a femur bone and used to fix a humerus, ulna, or radius bone structure. In a further example, a DBM derived from a femur can be used to repair vertebra.

In a further example, the bone can be derived from mammalian bone and used either allogeneically or xenogeneically. For example, DBM derived from human bones or skeletal structures can be used to treat human patients. In another example, DBM derived from bone structures of another mammalian species, such as bovine or porcine skeletal structures, can be used to treat human skeletal structures.

As illustrated at block 404, the bone matrix can be treated in a solution that includes a surfactant and a protease enzyme. In an example, protease includes subtilisin. In a further example, the protease can be included in the solution in an amount in a range of 0.01 wt % to 1.0 wt %. For example, the solution can include the protease in an amount in a range of 0.01 wt % to 0.5 wt %, such as a range of 0.01 wt % to 0.1 wt %.

In an example, the surfactant is an ionic surfactant, an amphoteric surfactant, or a non-ionic surfactant. The ionic surfactant can be an anionic surfactant. In another example, the ionic surfactant can be a cationic surfactant. An example anionic surfactant includes a sulfate surfactant, a sulfonate surfactant, a phosphate surfactant, a carboxylate surfactant, or any combination thereof. An example sulfate surfactant includes alkyl sulfates, such as ammonium lauryl sulfate, sodium lauryl sulfate, or a combination thereof; an alkyl ether sulfate, such as sodium laureth sulfate, sodium myreth sulfate, or any combination thereof; or any combination thereof. An example sulfonate surfactant includes an alkyl sulfonate, such as sodium dodecyl sulfonate; docusates such as dioctyl sodium sulfosuccinate; alkyl benzyl sulfonate; or any combination thereof. An example phosphate surfactant includes alkyl aryl ether phosphate, alkyl ether phosphate, or any combination thereof. An example carboxylic acid surfactant includes alkyl carboxylates, such as fatty acid salts or sodium stearate; sodium lauroyl sarcosinate; a bile acid salt, such as sodium deoxycholate; or any combination thereof.

An example cationic surfactant includes primary, secondary, or tertiary amines, quaternary ammonium surfactants, or any combination thereof. An example quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An example amphoteric surfactant includes a primary, secondary, or tertiary amine or a quaternary ammonium cation with a sulfonate, carboxylate, or phosphate anion. An example sulfonate amphoteric surfactant includes (3-[(3-cholamidopropyl)dimethylammonio]-1-propanesulfonate); a sultaine such as cocamidopropyl hydroxysultaine; or any combination thereof. An example carboxylic acid amphoteric surfactant includes amino acids, imino acids, betaines such as cocamidopropyl betaine, or any combination thereof. An example phosphate amphoteric surfactant includes lecithin. In a further example, the surfactant can be a non-ionic surfactant such as a polyethylene glycol-based surfactant.

In an example, the surfactant can include an anionic surfactant, such a sulfate surfactant. For example, the surfactant can include sodium dodecyl sulfate (SDS) or a dodecyl benzene sulfonic acid (DBSA) or a salt thereof. The solution can include the surfactant in a range of 0.05 wt % to 5.0 wt %, such as a range of 0.05 wt % to 1.5 wt % or a range of 0.05 wt % to 0.5 wt %.

Treating the bone matrix with the solution can include exposing the bone matrix to the solution for period of between 10 hours and 40 hours, such as a period of between 16 hours and 36 hours or a period of between 20 hours and 28 hours. As illustrated at block 406, the treated bone matrix can be washed, such as using deionized water or purified water.

The washed and treated bone matrix can be acid treated, as illustrated at block 408. For example, the bone matrix can be submersed in an acid solution that includes an acid, such as nitric acid, sulfuric acid, hydrochloric acid, or a combination thereof. In a particular example, the acid solution includes hydrochloric acid. The acid solution can include acid in a concentration in a range of 0.1 M to 3.0 M, such as a range of 0.3 M to 2.0 M, or a range of 0.5 M to 1.5 M. The acid solution can have a pH in a range of 0.5 to 5.0, such as a pH in a range of 0.5 to 3.0, a range of 0.5 to 2.5, or a range of 1.0 to 2.0. Treating the bone matrix in the acid solution can include treating for a period of between 12 hours and 72 hours, such as a period of between 20 hours and 56 hours or a period of between 32 hours and 50 hours.

Following acid treatment, the acid treated on matrix can be washed, as illustrated at block 410. For example, the acid treated bone matrix can be washed using deionized water (diH2O) or purified water.

As illustrated at block 412, the acid washed bone matrix can be electrophoretically treated in a surfactant solution. The surfactant solution and be in form of an aqueous fluid or can be in the form of a gel. The surfactant solution can include a surfactant as described above. In an example, the surfactant solution includes an ionic surfactant, such as a sulfate surfactant, for example, sodium dodecyl sulfate (SDS). The surfactant solution can include surfactant in an amount in a range of 0.5 wt % to 5.0 wt %, such as an amount in a range of 0.5 wt % to 2.0 wt %. The acid treated bone matrix can be electrophoretically treated for a period in a range of 2 hours to 12 hours, such as a range of 2 hours to 8 hours.

An electrophoretic apparatus used to treat that bone matrix can apply a potential across electrodes of the apparatus. The potential can be in a range of 20 V to 80 V, such as a potential in a range of 32 V to 64 V or a range of 40 V to 60 V. In particular, the electrophoretic device treating the acid treated bone matrix can apply potential and current at a power between 5 W and 30 W to the electrodes, such as 10 W to 25 W or 12 W to 18 W to the electrodes. Further, the apparatus can provide a current in a range of 100 mA to 500 mA, such as 200 mA to 400 mA or even 250 mA to 350 mA through the electrodes.

As illustrated at block 414, the treated demineralized bone matrix can be further washed, for example in deionized water. Optionally, during washing, the demineralized bone matrix can be exposed to the deionized water in the electrophoretic apparatus, which applies the above potential, power, or current to the electrodes of the apparatus and across the demineralized bone matrix in the presence of the deionized water to further wash the biomolecules, such as polynucleotide or biomarkers, and components of the surfactant solution from the demineralized bone matrix.

Figure 5:
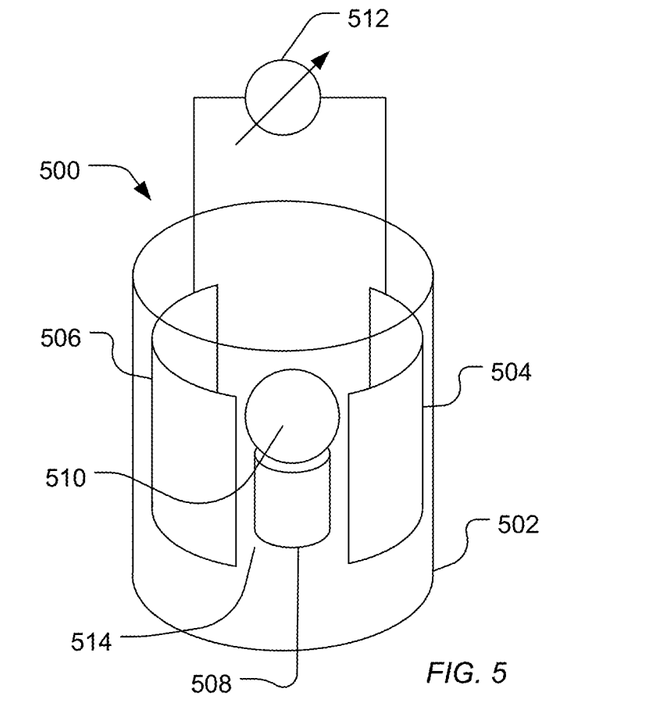
FIG. 5 includes an illustration of an example electrophoretic apparatus.

As illustrated in FIG. 5, an electrophoretic apparatus 500 includes at least two electrodes 504 and 506 disposed in a container 502. A tissue sample 510 is placed on a tissue holder 508 to secure the tissue sample 510 between the electrodes 504 and 506. An electric potential is provided across the electrodes 504 or 506, such as by a power source 512. Further, a composition 514 is placed within the container 502 in contact with the electrodes 504 or 506 and the tissue sample 510.

In an example, one or more of the electrodes 504 or 506 is formed of or coated with a corrosion-resistant conductive material. In example, the corrosion-resistant conductive material includes a metal, a ceramic material, a conductive polymeric material, or any combination thereof. An example corrosion-resistant conductive metal includes platinum, gold, silver, or any combination thereof. An example ceramic conductive material includes indium tin oxide, tungsten silicide, tantalum nitride, indium oxide, tungsten nitride, titanium nitride, titanium diboride, molybdenum silicide, silicon carbide, zirconia, tin oxide, lanthanum chromite, doped alumina, or any combination thereof. An example conductive polymeric material includes polyacetylene, poly(p-phenylene vinylene), polyfluorene, polyphenylene, polypyrene, polyazulene, polynaphthalene, polypyrrole, polycarbazole, polyindole, polyazepine, polyaniline, polythiophene, poly(3,4-ethylenedioxythiophene, poly(p-phenylene sulfide), or any combination thereof. In another example, the corrosion-resistant conductive material can include a conductive composite material including conductive particles in a polymeric matrix.

In an example, each of the electrodes 504 or 506 is formed of or coated with the same corrosion-resistant conductive material. Alternatively, the electrodes 504 or 506 can be formed of or coated with different corrosion-resistant conductive materials.

As illustrated in FIG. 5, the power source 512 is coupled to the electrode 504 and the electrode 506. In an example, the power source 512 provides a constant potential or voltage difference between the electrodes 504 or 506. In another example, the power source 512 provides an oscillating voltage difference between the electrodes 504 or 506, such as an alternating voltage difference between the electrodes 504 or 506. In a further example, the power source 512 can provide an oscillating voltage difference with a voltage bias between the electrodes 504 or 506. In particular, the power source 512 can supply a voltage difference in a range of 0.1 V to 200 V, such as a range of 1 V to 100 V, a range of 5 V to 90V, or even a range of 10 V to 60 V. Further, the power supply 512 can provide a current in a range of 0.05 amps to 5 amps, such as a range of 0.1 amps to 3 amps, a range of 0.1 amps to 2 amps, or even a range of 0.5 amps to 1 amp.

Figure 6:
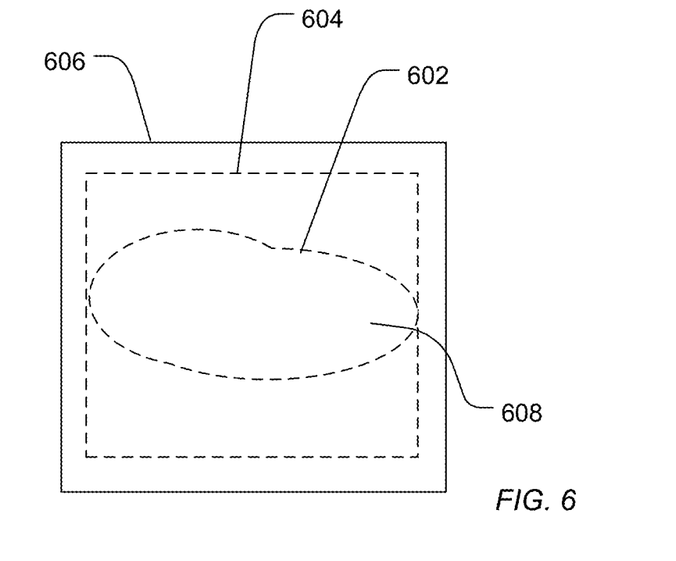
FIG. 6 includes an illustration of an example projection of a tissue sample on an electrode surface.

In an example, the electrodes 504 or 506 have a desirable surface area relative to the size of the projected surface area of the tissue sample 510. When viewing the tissue sample 510 through an electrode toward a different electrode, the tissue sample projects a perimeter, defining a projected area on the electrode. For example, as illustrated in FIG. 6, when viewing a tissue sample through an electrode 606, the tissue sample defines a perimeter 602 surrounding a projected area 608 projected onto the electrode 604 or 606. In particular, the surface area of the electrode 604 or 606 is at least 60% of the projected area of the tissue sample. For example, the surface area of the electrode can be at least 75% of the projected area, such as at least 90% of the projected area, or even at least 100% of the projected area. In a particular example, the surface area can be at least 115%, such as at least 130%, or even at least 150% of the projected area of the tissue sample. In a further example, the container can include physical restrictions, such as baffles, providing an effective cross-sectional area for current or ion flow. Such restrictions can effectively provide the surface area as described above.

Figure 8:
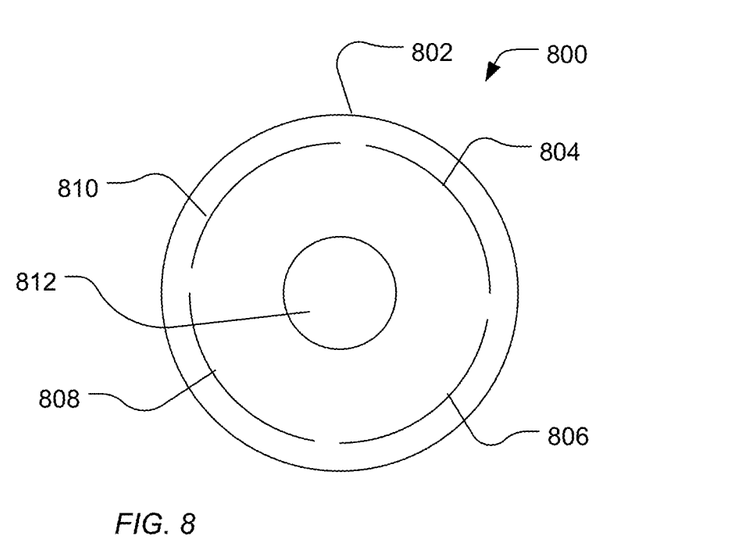
FIG. 8 includes an illustration of an example electrophoretic apparatus.

In a further example, the tissue holder 508 can rotate the tissue sample 510 by at least 90°. For example, the tissue holder 508 can rotate the tissue sample 510 by at least 180°. Alternatively, the electrodes 504 or 506 can be rotated around the sample by at least 90°, such as at least 180°. In a further alternative example, the electrophoretic apparatus 500 can include additional electrodes. For example, as illustrated in the top view of FIG. 8, the electrophoretic apparatus 800 can include at least four electrodes 804, 806, 808, and 810, surrounding a tissue sample 812 in a container 802. Each opposing pair of electrodes can be activated with a relative electric potential that is either constant, oscillating, or both.

Returning to FIG. 5, the space disposed between the electrodes 504 and 506 in which the tissue sample 510 is disposed includes a composition or solution in contact with the electrodes 504 or 506 and the tissue sample 510. The composition can be a liquid composition. In an alternative example, the composition can be a hydrogel composition. For example, the hydrogel can be formed of an agarose gel, a polyacrylate, a polyacrylamide gel, or any combination thereof. In particular, the hydrogel can include 0.1% to 5% (w/v) of an agarose or polymer component.

In an example, the composition or solution is a buffered composition having a desirable pH in a range of 6.5 to 8.5. For example, the pH of the composition can be in a range of 7.0 to 8.0. In an example, the composition is buffered with an agent, such as a carboxylic acid, a phosphate salt such as monopotassium phosphate or diammonium phosphate, or any combination thereof.

Further, the composition or solution includes a surfactant. For example, the composition can include a surfactant in an amount of 0.01 wt % to 10 wt %, such as a range of 0.01 wt % to 7 wt %, a range of 0.05 wt % to 5 wt %, or even a range of 0.1 wt % to 5 wt %.

In an example, the surfactant can be selected from the surfactants described above. In a particular example, the surfactant is an ionic surfactant, such as an anionic surfactant. An example anionic surfactant includes a sulfate surfactant, a sulfonate surfactant, a phosphate surfactant, a carboxylate surfactant, or any combination thereof. An example sulfate surfactant includes alkyl sulfates, such as ammonium lauryl sulfate, sodium lauryl sulfate, or a combination thereof; an alkyl ether sulfate, such as sodium laureth sulfate, sodium myreth sulfate, or any combination thereof; or any combination thereof. An example sulfonate surfactant includes an alkyl sulfonate, such as sodium dodecyl sulfonate; docusates such as dioctyl sodium sulfosuccinate; alkyl benzyl sulfonate; or any combination thereof. An example phosphate surfactant includes alkyl aryl ether phosphate, alkyl ether phosphate, or any combination thereof. An example carboxylic acid surfactant includes alkyl carboxylates, such as fatty acid salts or sodium stearate; sodium lauroyl sarcosinate; a bile acid salt, such as sodium deoxycholate; or any combination thereof. In an example, the surfactant is a dodecyl sulfate salt, dodecyl sulfonate salt, or dodecyl benzyl sulfonic acid salt, or any combination thereof.

In particular, the composition or solution can be provided by perfusion through natural conduits in the bone matrix, such as remnants of vascularity or porosity. For example, the electrophoresis apparatus can include a perfusion pump and one or more tubes or needles to perfuse the composition into the sample. Absent a vascular system or porosity, the composition can be supplied using a circulation of the reagents in the chamber or by direct injection into the tissue using a needle or cannula. Any of the circulation method, the direct injection method, or the perfusion method can be performed using magnetic driven, peristaltic, sinusoidal, or pneumatic pumps, such as diaphragm, reciprocating, plunger, piston, or high-pressure pneumatic pumps.

Figure 7:
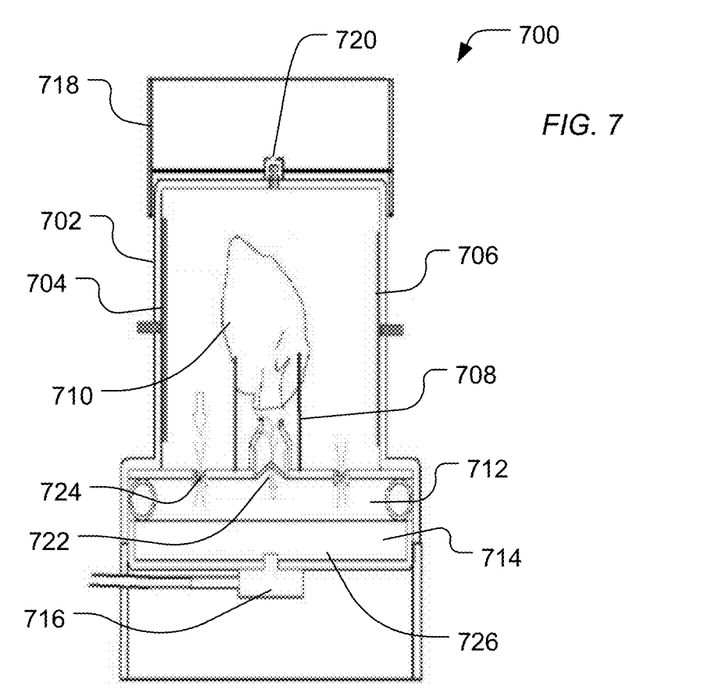
FIG. 7 includes an illustration of an example electrophoretic apparatus.

Turning to FIG. 7, an electrophoretic apparatus 700 includes a container 702, in which at least two electrodes 704 and 706 are disposed. A tissue support 708 supports a tissue sample 710 between the at least two electrodes 704 or 706. The electrophoretic apparatus 700 can also include a degassing or pressure release valve 720 and a capture container 718 to capture gas escaping through the degassing valve 720.

When the composition is a liquid, a liquid can be circulated using a pump 726 and valves 722 and 724. For example, the pump 726 can include a fluid chamber 712, a diaphragm 714 and a pressure source 716. The pressure source 716 can change pressure to drive the diaphragm 714 to push fluid from the chamber 712 through an outlet valve 722 positioned under the tissue support 708. Pressure can be removed from the diaphragm 414 and fluid can be drawn from the chamber 702 through outlet valve 724.

Alternatively, the composition or solution can be provided by perfusion through remnants of a vascular system or porosity. In another alternative, the composition can be provided by direct injection, such as through a cannula or needle. For any of the circulation method, the direct injection method, or the perfusion method, the illustrated pump 726 can be replaced with a magnetic driven, peristaltic, sinusoidal, or pneumatic pump, such as a diaphragm, reciprocating, plunger, piston, or high-pressure pneumatic pumps.

In operation, a bone matrix 710 is placed on support 708 within the chamber 702. A composition is provided to the chamber 702 to contact the electrodes 704 and 706 and tissue sample 710. Electrodes 704 or 706 can be sized to cover at least 60% of the projected area the tissue sample 710. In example, the composition is a buffered liquid solution having a pH in a range of 6.0 to 8.5. Further, the composition can include a surfactant, such as an anionic surfactant.

A voltage potential can be applied across the electrodes 704 or 706 using an external power source. In an example, the power source provides a constant voltage potential across the electrodes 704 or 706. In a further example, the power source can provide a constant current between electrodes 704 or 706. In an additional example, the power source can provide an oscillating voltage potential across the electrodes 704 and 706, such as an alternating voltage potential across the electrodes 704 and 706. In a further embodiment, the power source can provide an oscillating voltage potential across electrodes 704 and 706 with a constant bias.

While the voltage difference is applied across electrodes 704 or 706, a pump can be activated to provide a composition through the inlet valve 722 and to draw the composition through outlet valves 724. In such a manner, the composition can be circulated. Alternatively, the composition can be perfused through vasculature or porosity of the bone matrix. While the composition is illustrated as flowing in and out of a single diaphragm pump, alternatively, the composition can be drawn from the electrophoretic apparatus 700, filtered, buffered, and resupplied to the chamber 702. The temperature during electrophoresis can be not greater than 35 C, such as not greater than 30 C, not greater than 28 C, or not greater than 26 C. In particular, the temperature is at least 15 C.

Optionally, the tissue holder 708 can rotate the bone matrix 710 by at least 90°. For example, the tissue holder 708 can rotate the bone matrix 710 by at least 180°. Alternatively, the electrodes 704 or 706 can be rotated around the bone matrix 710 by at least 90°, such as at least 180°. In a further alternative example, the electrophoretic apparatus 700 can include additional electrodes. For example, the electrophoretic apparatus 700 can include at least four electrodes surrounding the tissue sample 710. Each opposing pair of electrodes can be activated with a relative electric potential that is either constant, oscillating, or both.

In particular, the treatment time is inversely proportional to the electrode surface area, electrode potential, decellularization strength of the solution and directly proportional to the amount of tissue, and distance between the electrodes. As such, $$T_d \text{ is proportional to } (V_t \times D_e)/(A_e \times P_e \times S_s)$$

wherein, $T_d$ is the decellularization time, $V_t$ is the tissue volume, $D_e$ is the distance between electrodes, $A_e$ is the area of electrodes, $P_e$ is the electric potential across the electrodes, and $S_s$ is the surfactant strength.

Once a treatment is complete, the demineralized bone matrix (DBM) can be removed from the electrophoretic apparatus 700. Such a bone matrix can be washed, sterilized, treated, and repopulated with cells. For example, cells from the patient can be used to repopulate the DBM in vitro. In an alternative example, the DBM can be implanted into a patient and the patient's cells can repopulate the DBM in vivo.

Figure 9:
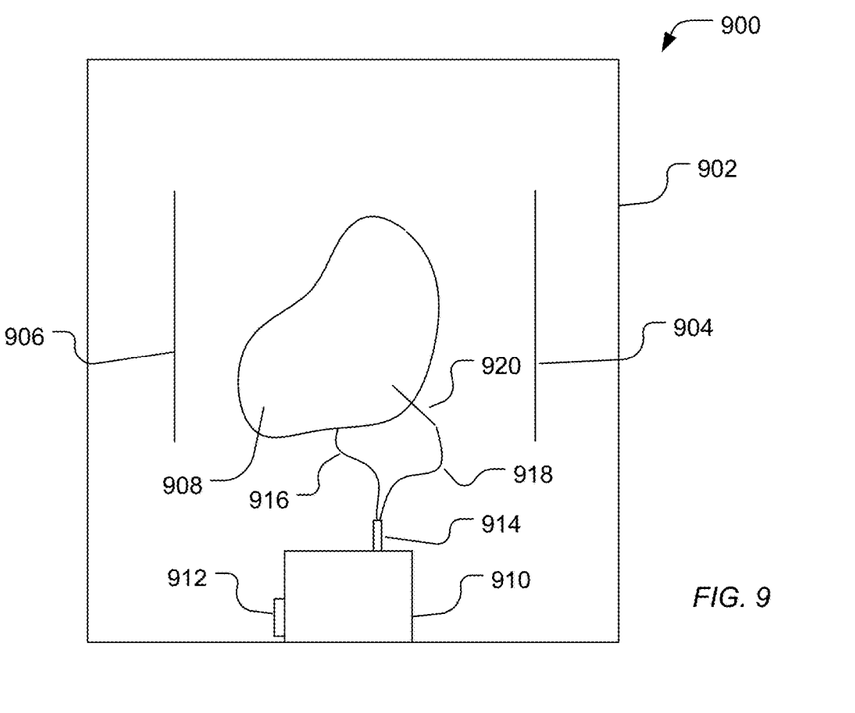
FIG. 9 includes an illustration of an example electrophoretic apparatus.

In a further example, the electrophoretic apparatus, such as the device 700, can further include a perfusion pump and one or more conduits connected to the perfusion pump to provide a solution into the tissue. For example, FIG. 9 illustrates a device 900 that includes a container 902 and a bone matrix 908 disposed between two electrodes 904 and 906. The device 900 also includes a perfusion pump 910 having an inlet 912 and one or more outlets 914. As illustrated, the perfusion pump 910 can be disposed in the container 902 and electrophoretic composition and solution can be collected by the inlet 912 and pumped through the outlet 914. Alternatively, the perfusion pump 910 can be external to the container 902 and can receive electrophoretic solution from the container 902 through an inlet tube or can obtain solution from an external source. In a further example, the solution or composition pumped through the perfusion pump 910 can be different than the solution or composition within the container.

One or more conduits, such as tubes or hoses, can be connected to the outlet 914 of the perfusion pump 910. For example, a tube 916 can be connected to the outlet 914 at one end and can be connected to the tissue 908 at the other end by suture, cannulation, or another mechanism to a vascular structure of the tissue 908. In another example, a tube 918 can be connected to the outlet 914 and can be connected to a needle or cannula 920 to inject solution into the matrix 908. In a further example, a tube can be connected to the outlet 914 and to a perfusion tube disposed within the matrix. A perfusion tube permits solution to permeate the tube walls and enter the porosity of the matrix. An example perfusion tube includes a woven tube structure or stent-like structure.

Figure 10:
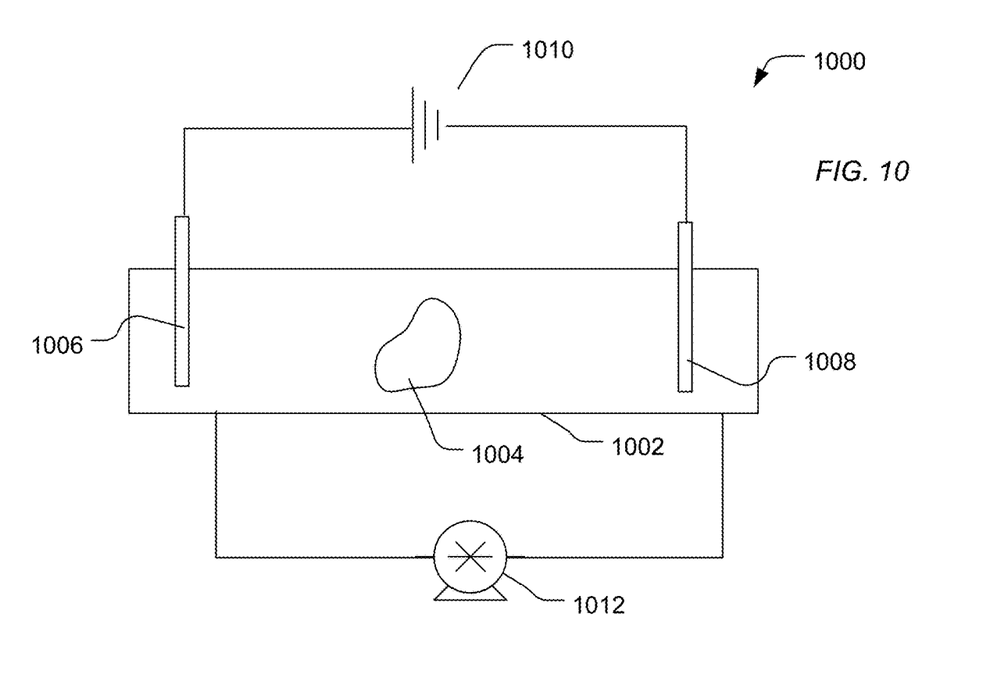
FIG. 10 includes an illustration of an example electrophoretic apparatus.

In another example, an electrophoretic apparatus 1000 illustrated in FIG. 10 includes a container 1002 into which an electrophoretic solution and the bone matrix 1004 can be applied. The apparatus further includes two electrodes 1006 and 1008 across which a potential can be applied by a power source 1010. Optionally, a pump 1012 can circulate the electrophoretic solution through the chamber. In a particular example, the electrophoretic solution can be cleaned, filtered, and recirculated using the pump 1012. In an alternative example, the electrophoretic solution can be a gel.

The electrophoresis apparatus can include a platinum wire anode and an aluminum plate cathode. The electrophoretic apparatus can also include a filter cartridge in chamber.

In an example, the chamber combines an approximately uniform electric field potential across the matrix with fluid circulation resulting in efficient cleaning of xenogeneic bone matrices of various volume, shapes, and weights. The resulting DBM can transmit physiologically relevant forces to tendons, providing a degradable collagen-based platform for incursion by bone progenitors, porosity, or versatility to customize delivery of growth factors, cytokines, and chemokines to improve regeneration. Large volume DBMs produced by the electrophoretic apparatus and the above method can have the appropriate mechanical properties for short term therapeutic benefits and long-term bone regrowth.

In particular, the above methods can remove polynucleotides, biomarkers and antigens that causes tissue graft rejection.

The DBM has a DNA content of not greater than 0.1 micrograms per milligram sample. In an example, the DNA content is in a range of 0.01 micrograms per milligram sample to 0.1 micrograms per milligram sample. For example, the DNA content is in a range of 0.01 micrograms per milligram sample to 0.05 micrograms per milligram sample, such as a range of 0.01 micrograms per milligram sample to 0.45 micrograms per milligram sample.

In another example, the DBM has an alpha-gal (galactose-alpha-1,3-galactose) content in a range of 0.005 ng/ml to 0.5 ng/ml. For example, the DBM has an alpha-gal content in a range of 0.005 ng/ml to 0.3 ng/ml, such as in a range of 0.01 ng/ml to 0.2 ng/ml or in a range of 0.01 ng/ml to 0.1 ng/ml.

In an example, the DBM has collagen I in an amount of 0.5 mg/g wet sample to 1.1 mg/g wet sample. For example, the DBM has collagen I in an amount of 0.7 mg/g wet sample to 1.0 mg/g wet sample, such as in an amount of 0.8 mg/g wet sample to 1.0 mg/g wet sample. Treatment of the DBM can advantageous retain collagen structures. For example, the DBM can retain at least 85% collagen I when compared to untreated samples. In an example, the DBM retains at least 88% collagen I, such as at least 90% collagen I or at least 91% collagen I when compared to an untreated sample. The DBM can retain not greater than 100% collagen I, such as not greater than 99%, not greater than 98%, or not greater than 97%.

In an example, the DBM has a Young's Modulus in a range of 150 kPa to 300 kPa. For example, the DBM can have a Young's Modulus in a range of 180 kPa to 280 kPa, such as a range of 180 kPa to 250 kPa, a range of 190 kPa to 220 kPa, or a range of 200 kPa to 215 kPa.

More generally, a DBM supports a number of functions beyond simple structural support including controlling the chemical and mechanical microenvironment, sequestering, and presenting active growth factors, and mediating cell-cell contact. Once formed, the DBM can be repopulated with stem cells.

Stem cells include a population of cells that has the ability to self-renew and to differentiate into one or more specialized mature cell types. The classification of stem cells is often dependent on their species and tissue of origin and their differentiation potential into mature cell type(s). Stem cells isolated from various sources can vary in their differentiation capacity or pluripotentiality. Such differentiation capacity is thought to be an indication of cellular differences in the organisms, the ontogenic stage of the stem cell or the environmental conditions to which the stem cell is exposed. Two primary groups of stem cells have been defined, to date. The first group, embryonic stem cells (ESCs), is believed to have an indefinite replicative capacity and the ability to generate somatic cells of the body. The second population of stem cells is denoted as adult stem cells, which have been characterized from adherent and non-adherent fractions of bone marrow, adipose tissue, as well as specific organs. Such cells can be expanded in clinically relevant proportions and can be autologous. Stem cells can be isolated from a patient's own bone or adipose and prepared for infusion within 1-2 hours.

The transmission of mechanical force by DBM generally regulates cellular responses, extending from basic processes of engraftment, such as motility and spreading, to differentiation. When myotubes are grown on DBM substrates, they striate only on compliant surfaces that mimic the normal force transmission found in muscle. Specific matrix stiffness can lead to specification of a specific lineage, including neuronal, muscle or osteoblasts. Such specification results in stable programming of the cells that cannot be reprogrammed by altering either the mechanical or cytokine environment. As such, stem cells can be preconditioned for tissue engineering.

EXAMPLES

Example 1

A demineralized bone matrix is formed from a mammalian bone sample, in particular a porcine mandible.

Figure 11:
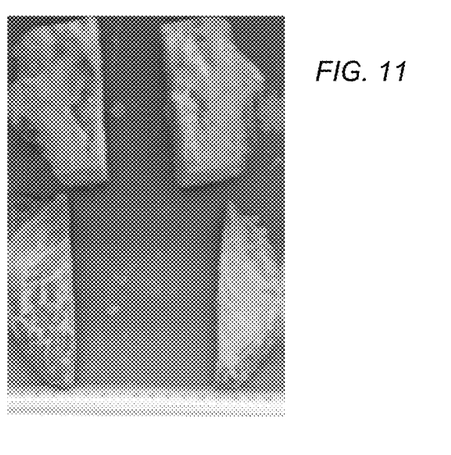
FIG. 11, FIG. 12, FIG. 13, FIG. 14, FIG. 15, and FIG. 16 include images illustrating process steps of a treatment method.

The frontal skull and mandible is removed from below the masseter muscle from a porcine skull bone using a hacksaw, surgical scissors, and bone shears. Extraneous tissues are cleaned from the bone samples using a sterile scalpel. One skull yields four samples (two mandible samples and one frontal skull sample divided into two) illustrated in FIG. 11.

Figure 12:
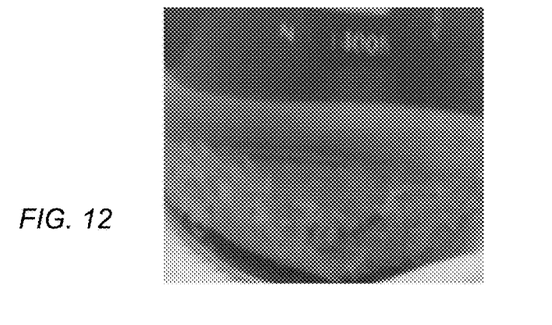

Each sample is soaked in 500 ml of a 10% detergent solution at room temperature (22 C) for 24 hours, as illustrated in FIG. 12. The detergent solution includes 50.0 mL Liquid Biz Detergent and 450 mL of deionized water (diH2O). Following soaking, the samples are removed from the detergent solution and washed with diH2O, three times.

Figure 13:
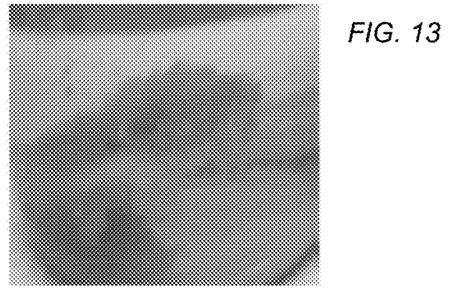
Figure 14:
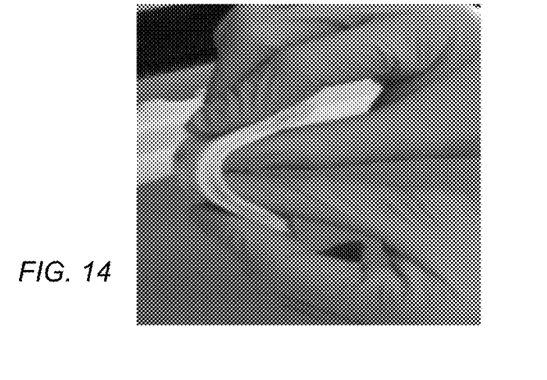

The samples are soaked in 500 ml of a 0.9 M HCl solution for 24 hours, as illustrated in FIG. 13. The HCl solution is made using 12 M HCl stock. An amount of 37.5 ml stock 12M HCl is added to 462.5 ml dH2O. The samples are removed and soaked in 500 ml 2.4 M HCl solution for 24 hours for mandible samples of less than 1 cm in width. If the sample is greater than 1.5 cm, which is typical for frontal skull samples, the samples are soaked in 500 ml 2.4 M HCl solution for 48 hours. Following soaking, the samples are flexible. The 2.4 M HCl solution is formed by adding 100 ml stock 12M HCl to 400 ml diH2O. FIG. 14 illustrates how flexible a mandible sample is 24 hours post soaking in a 2.4 M HCl solution. Note frontal skull samples can take 48 hours to reach this flexibility.

Figure 15:
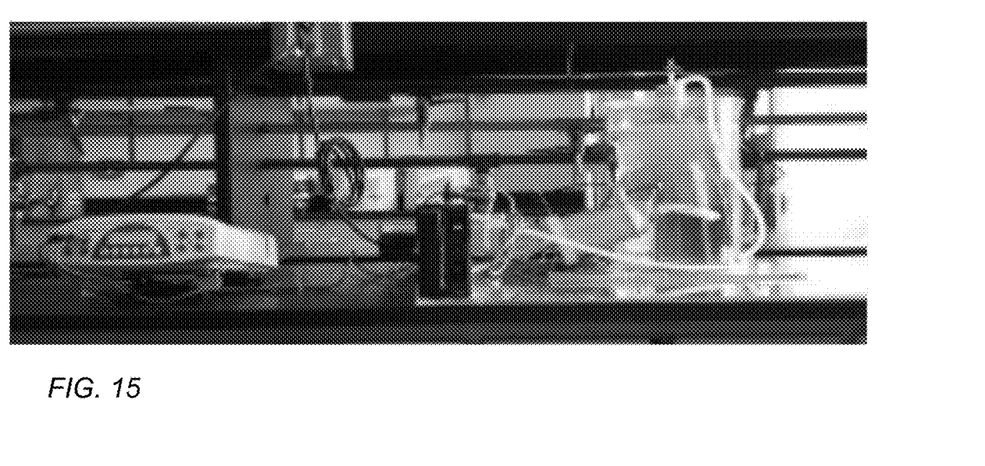

The samples are electrophoretically treated in a Fabrico electrophoresis chamber in 8.0 L of 1% w/v sodium dodecyl sulfate (SDS) solution for 6 hours at 50 volts and 15 watts (300 mA) and maintaining a temperature of the solution in a range of 24 C to 25 C (see, FIG. 15). The electrophoresis chamber/apparatus includes a platinum wire anode and an aluminum plate cathode. The aluminum electrode is replaced every two runs and the platinum electrode is replaced as needed. A filter cartridge in chamber is replaced every 5 runs. The samples are suspended in the chamber by puncturing a hole with an awl and feeding through appropriate length nylon line. The SDS solution is formed from 80 g of powdered SDS and water to make 8.0 L of 1% w/v SDS solution. The samples are treated in the electrophoresis chamber/apparatus for 6 hours.

Figure 16:
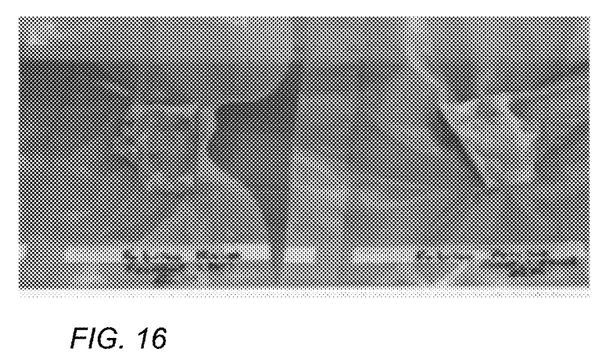

The samples are further exposed to a post electrophoretic treatment, in which the samples are removed from the chamber and rinsed for 5 minutes with diH2O. The 1% SDS solution is removed from the electrophoretic chamber, and the chamber is rinsed with diH2O. The electrophoresis chamber is filled with 8 L of diH2O, and the samples are inserted into the chamber and treated at 50 V and 300 mA in diH2O for 15 minutes to remove SDS. The diH2O is removed and the chamber is rinsed again with diH2O for 5 minutes. The samples are stored in vacuum seal package at −20 C (see FIG. 16.).

Example 2

A total DNA analysis of decalcified and electrophoretically decellularized bioscaffold porcine bone matrix is performed.

Control (untreated) and decalcified/decellularized porcine mandible and frontal skull samples prepared using the procedure of Example 1 are assayed to assess the efficacy of decellularization and the removal of DNA and other biomarkers. The samples are analyzed for total DNA extraction using the DNaesy Blood & Tissue Kit (Qiagen, Valencia, Calif.). Total DNA is used as an indication of decellularization of porcine cells from the porcine bone. Samples are ground using a homogenizer (Mini-Beadbeater-16 homogenizer Biospec Products Bartlesville, Okla.). The samples are lysed using proteinase K and proprietary extraction buffers provided by the kit. The lysate is loaded onto miniprep spin columns and buffer is added that is previously adjusted to provide preferred DNA-binding conditions. During centrifugation, DNA is selectively bound to the DNeasy membrane as contaminants passed through. Remaining contaminants and enzyme inhibitors are removed in two wash steps, and DNA is then eluted into buffer. Subsequently, DNA quantification is performed by a Shimadzu UV/Vis 1240 mini Spectrophotometer (Shimadzu USA, Columbia, Md., USA) using OD260/OD320 data. Data for total DNA extraction is presented below in Table 1. Total μg DNA extracted/mg of sample data is calculated by the following formulas:

Concentration (μg/mL)=($A260$–$A280$)×(Dilution factor 50)×(50 μg/mL for pure dsDNA at $A280$)

Total μg DNA extracted/mg of sample=conc. (μg/mL)×0.200 ml (total volume of sample)]/mass of sample (mg)

TABLE 1

| | | Mean total micrograms of procine DNA extracted per | | | | | | | | | |
|---|---|---|---|---|---|---|---|---|---|---|---|
| Sample | Identity | Mass of Sample (mg) | Absorbance at 260 nm | Absorbance at 320 nm | Dilution Factor (20 μL to 980 μL H2O) | A260 of 1.0 = 50 μg/ml pure dsDNA | ds DNA concentration (μg/mL) | total volume of sample (mL) | total μg DNA extracted | total μg DNA extracted/ mg of sample | | |
| 1 | Control-1 | 150 | 0.077 | 0.007 | 50.0 | 50.0 | 175.0 | 0.200 | 35.00 | 0.2333 | mean control | 0.1817 |
| 2 | Control-2 | 170 | 0.065 | 0.001 | 50.0 | 50.0 | 160.0 | 0.200 | 32.00 | 0.1882 | SD control | 0.0552 |
| 3 | Control-3 | 170 | 0.042 | 0.000 | 50.0 | 50.0 | 105.0 | 0.200 | 21.00 | 0.1235 | | |
| 4 | Mandible-1 | 180 | 0.025 | 0.012 | 50.0 | 50.0 | 32.5 | 0.200 | 6.50 | 0.0361 | mean Mandible | 0.0422 |
| 5 | Mandible-2 | 230 | 0.018 | 0.009 | 50.0 | 50.0 | 22.5 | 0.200 | 4.50 | 0.0196 | SD Mandible | 0.0262 |
| 6 | Mandible-3 | 240 | 0.042 | 0.008 | 50.0 | 50.0 | 85.0 | 0.200 | 17.00 | 0.0708 | | |

TABLE 1-continued

Mean total micrograms of procine DNA extracted per

| Sample | Identity | Mass of Sample (mg) | Absorbance at 260 nm | Absorbance at 320 nm | Dilution Factor (20 µL to 980 µL H2O) | A260 of 1.0 = 50 µg/ml pure dsDNA | ds DNA concentration (µg/mL) | total volume of sample (mL) | total µg DNA extracted | total µg DNA extracted/ mg of sample | | |
|---|---|---|---|---|---|---|---|---|---|---|---|---|
| 7 | Frontal Skull-1 | 220 | 0.022 | 0.003 | 50.0 | 50.0 | 47.5 | 0.200 | 9.50 | 0.0432 | mean Frontal Skull | 0.0460 |
| 8 | Frontal Skull-2 | 230 | 0.012 | 0.007 | 50.0 | 50.0 | 12.5 | 0.200 | 2.50 | 0.0109 | SD Frontal Skull | 0.0398 |
| 9 | Frontal Skull-3 | 200 | 0.038 | 0.002 | 50.0 | 50.0 | 90.0 | 0.200 | 18.00 | 0.0900 | | |

TABLE 2

One-way ANOVA results table for mean total µg DNA extracted/mg of DBM sample for control, mandible, and frontal skull samples.

Number of Groups (k) 3
Level of Significance 0.05
RESULTS

| Group | n | Mean | Std Dev | | |
|---|---|---|---|---|---|
| Control | 3 | 0.1817 | 0.0552 | | |
| Mandible | 3 | 0.0422 | 0.0262 | | |
| Frontal Skull | 3 | 0.0480 | 0.0398 | | |
| Source | SS | df | MS | F | P |
| Between | 0.0374 | 2 | 0.0187 | 10.5499 | 0.0109 |
| Error | 0.0106 | 6 | 0.0018 | | |
| Total | 0.0480 | 8 | | | |

Figure 17:
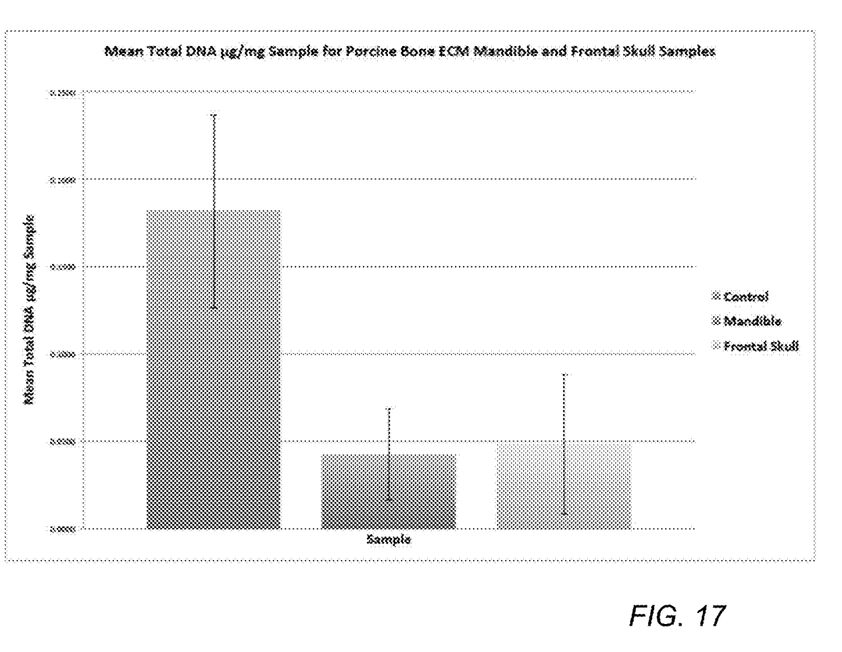
FIG. 17 includes a graph illustration of DNA content in samples.

Mean total µg DNA extracted per mg of sample data was analyzed using a one-way ANOVA test. One-way ANOVA test results and graph are show below in Table 2 and FIG. 17. One-way ANOVA results indicate a statistically significant difference (P<0.05) in the mean µg DNA/mg between control and mandible and control and frontal skull samples (P=0.0109). No statistically significant difference was observed between the mandible and frontal skull samples. These data indicate that the method of Example 1 is effective at removing porcine DNA from both mandible and frontal skull samples.

Example 3

A total alpha-gal analysis of decalcified and electrophoretically decellularized bioscaffold porcine bone matrix is performed.

Control (untreated) and decalcified/decellularized porcine mandible samples prepared using the procedure of Example 1 are assayed for the protein alpha-gal using the Alpha-Gal ELISA Kit from MyBioSource (San Diego, Calif., USA). Alpha-Gal was selected as a protein to assay because the xenoantigen alpha-gal is considered a major hindrance to the success of extracellular matrices in xenotransplantation.

Samples are homogenized using a Mini-Beadbeater-16 homogenizer (Biospec Products Bartlesville, Okla.). Next, proteins are extracted from the samples using extraction buffers provided by the kit. Standards for comparison are also prepared. An amount of 100 µL of each standard and sample are added to wells of a 96 well plate pre-coated by the ELISA kit's manufacturer with antibody to alpha-gal. The plates are incubated for 90 minutes at 37 C, then washed three times and a secondary antibody to alpha-gal was added to each well. Control and treatment samples are then incubated at 37 C for 60 minutes and subsequently washed three times.

Enzyme-conjugate is then added to each well and incubated for 30 minutes at 37 C. After incubation, wells are washed four times. A color reagent is added to each well, and when a color gradient for standards appears the reactions are quenched and the 96 well plate is read at 450 nm using a xMark Microplate Absorbance Spectrophotometer (BioRad, Hercules, Calif., USA). Data is adjusted for blank absorbance. A linear regression is determined using standards prepared from the Alpha-Gal ELISA Kit from MyBioSource (San Diego, Calif., USA). Absorbance measurements are illustrated in Table 3.

Figure 18:
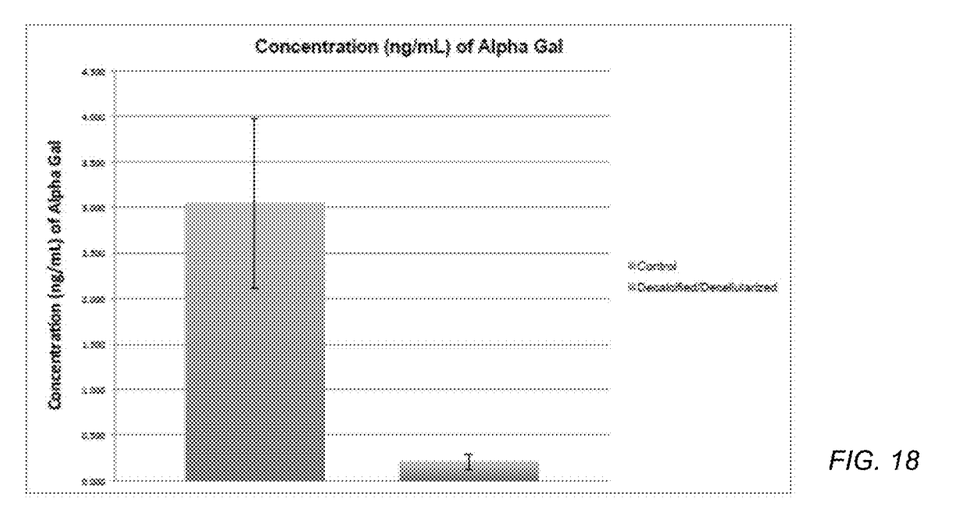
FIG. 18 includes a graph illustration of alpha-gal (galactose-alpha-1,3-galactose) concentration in samples.

Concentration (ng/ml) of alpha-gal is determined for control and treatment samples, as illustrated in Table 4 and FIG. 18. Mean and SD for sample sets are calculated and statistically compared using a t-test.

TABLE 3

Adjusted Absorbance for Standards, Controls, and Test Samples.

| Sample | Reference on 96 well plate | Raw Absorbance at 450 nm | Adjusted Absorbance at 450 nm less standard 8 blank or 0 ng/mL |
|---|---|---|---|
| Standard 1 | A1 | 1.983 | 1.938 |
| Standard 2 | B1 | 1.459 | 1.414 |
| Standard 3 | C1 | 0.850 | 0.805 |
| Standard 4 | D1 | 0.476 | 0.431 |
| Standard 5 | E1 | 0.321 | 0.276 |
| Standard 6 | F1 | 0.242 | 0.197 |
| Standard 7 | G1 | 0.138 | 0.093 |
| Standard 8 | H1 | 0.045 | 0.000 |
| Control 1 | A2 | 0.728 | 0.683 |
| Control 2 | B2 | 1.148 | 1.103 |
| Control 3 | C2 | 0.525 | 0.480 |
| Test 1 | D2 | 0.274 | 0.229 |
| Test 2 | E2 | 0.217 | 0.172 |
| Test 3 | F2 | 0.238 | 0.193 |

TABLE 4

Concentration of alpha-gal (ng/ml) for Control and Test Samples.

| Sample | Absorbance at 450 nm | Concentration (ng/mL) based on linear regression |
|---|---|---|
| Control 1 | 0.683 | 2.678 |
| Control 2 | 1.103 | 4.823 |
| Control 3 | 0.480 | 1.641 |
| Test 1 | 0.229 | 0.359 |
| Test 2 | 0.172 | 0.068 |
| Test 3 | 0.193 | 0.175 |

TABLE 4-continued

Concentration of alpha-gal (ng/ml) for Control and Test Samples.

|  | Control | Test |
|---|---|---|
| mean | 3.047 | 0.201 |
| SD | 1.623 | 0.147 |
| SEM | 0.937 | 0.085 |

Analysis of the t-test results for the comparison of mean concentration (ng/ml) of alpha-gal between control and treatment indicate that the means vary at a statistically significant level (P=0.0389). Mean treatment value of alpha-gal (0.201 ng/ml SD 0.147) indicates a 93.40% reduction in the amount of alpha-gal (ng/ml) compared to control porcine mandible samples (mean=3.047 ng/ml SD 1.623). These data suggest that the methods and procedures of EXAMPLE 1 remove alpha-gal from porcine bone mandible samples.

Example 4

A total collagen analysis of bioscaffold porcine bone matrix is performed.

The total collagen analysis of our porcine bone matrix is performed using the Total Collagen Assay Kit from BioVision (Milpitas, Calif. USA Catalog #K218-100). The assay is based on the acid hydrolysis of samples to form hydrolysates and hydroxyproline. The released hydroxyproline is oxidized to form a reaction intermediate, which further in the reaction, forms a chromophore (maximum absorbance at A560 nm). The assay is sensitive and specific for collagen I and can detect as low as 0.5 μg of collagen I in a sample.

For total collagen I analysis, three random samples are taken from a porcine bone mandible DBM prepared using the procedure of EXAMPLE 1.

Three positive control samples are randomly taken from an unprocessed porcine mandible bone. The samples are homogenized in sterile diH2O using a sterile scalpel and bone shears. The samples are mixed with an equal volume of 12 M HCl. Three negative controls using equal volumes of diH2O and 12 M HCl are prepared. Standards of 2, 4, 6, 8, and 10 μg collagen I are also prepared according to the manufacturer's protocol.

All samples and standards are incubated at 120 C for 3 hours to hydrolyze. Next, reagents Chloramine T and DMAB are added to the samples according to the manufacturer's protocol. All samples are then read at 560 nm using an xMark Microplate Reader (Bio-Rad Hercules, Calif. USA). Standard data is used to generate a linear regression. The total amount of collagen I in the samples, positive control, and negative control samples is quantified from the linear regression and normalized to wet mass of tissue sampled. See Table 5.

TABLE 5

Absorbance of Standard, Positive Control, Negative Control, and Test Samples.

| Sample | Reference on 96 well plate | Raw Absorbance at 560 nm | Adjusted Absorbance at 560 nm less standard 1 blank or 0 μg collagen I | Wet Mass Sample (g) |
|---|---|---|---|---|
| Standard 1 (0 μg) | A1 | 0.112 | 0.000 | |
| Standard 2 (2 μg) | A2 | 0.127 | 0.015 | |
| Standard 3 (4 μg) | A3 | 0.136 | 0.024 | |
| Standard 4 (6 μg) | A4 | 0.159 | 0.047 | |
| Standard 5 (8 μg) | A5 | 0.189 | 0.077 | |
| Standard 6 (10 μg) | A6 | 0.201 | 0.089 | |
| Positive Control 1 | B1 | 1.789 | 1.677 | 0.170 |
| Positive Control 2 | B2 | 1.397 | 1.285 | 0.200 |
| Positive Control 3 | B3 | 1.827 | 1.715 | 0.190 |
| Negative Control 1 | C1 | 0.11 | −0.002 | 0.000 |
| Negative Control 2 | C2 | 0.111 | −0.001 | 0.000 |
| Negative Control 3 | C3 | 0.109 | −0.003 | 0.000 |
| ECM Test 1 | D1 | 1.19 | 1.078 | 0.140 |
| ECM Test 2 | D2 | 0.984 | 0.872 | 0.160 |
| ECM Test 3 | D3 | 1.21 | 1.098 | 0.110 |

TABLE 6

Collagen I in Control and Test Samples.

| Sample | Absorbance at 560 nm | Total amount Collagen I (μg) based on linear regression | Total amount Collagen I (mg) | Total amount of Collagen I mg/g wet sample |
|---|---|---|---|---|
| Positive Control 1 | 1.677 | 179.817 | 0.180 | 1.058 |
| Positive Control 2 | 1.285 | 137.667 | 0.138 | 0.688 |
| Positive Control 3 | 1.715 | 183.903 | 0.184 | 0.968 |
| Negative Control 1 | −0.002 | 0.000 | 0.000 | 0.000 |
| Negative Control 2 | −0.001 | 0.000 | 0.000 | 0.000 |
| Negative Control 3 | −0.003 | 0.000 | 0.000 | 0.000 |
| ECM Test 1 | 1.078 | 115.409 | 0.115 | 0.824 |
| ECM Test 2 | 0.872 | 93.258 | 0.093 | 0.583 |
| ECM Test 3 | 1.098 | 117.559 | 0.118 | 1.069 |

|  | Pos. Control | Neg. Control | ECM Test |
|---|---|---|---|
| mean | 0.905 | 0.000 | 0.825 |
| SD | 0.193 | 0.000 | 0.243 |
| SEM | 0.111 | 0.000 | 0.140 |

Figure 19:
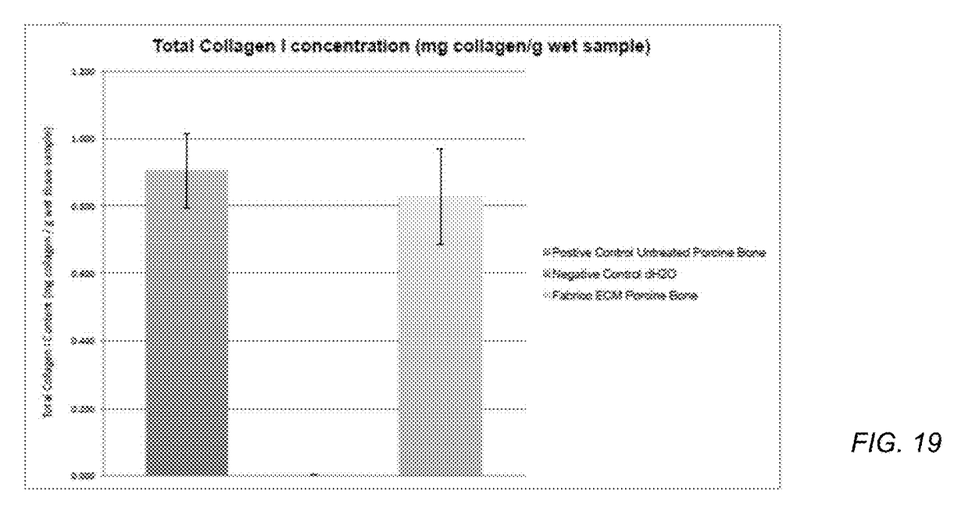
FIG. 19 includes a graph illustration of collagen I content samples.

The data illustrated in Table 6 and FIG. 19 indicate that the porcine mandible bone DBM retains 91.16% of collagen I post-decalcification and decellularization compared to untreated porcine bone samples. The sample porcine bone DBM had a total collagen I (mean=0.905 mg collagen/g wet sample, SD=0.193) compared to untreated porcine bone samples (mean=0.905 mg collagen/g wet sample, SD=0.193). Collagen is a primary constituent of bone and provides the structural stability to engineer bone scaffolds for tissue regeneration. The sample DBM also retain natural microarchitecture, which may provide additional advantages as a biological scaffold for bone regeneration.

Example 5

Load is applied to the center of the sample DBM by a load rod having a radius of 0.3 cm. The ring support has a diameter of 3.0 cm. Load is applied in 10 uniform increments until a maximum deflection of 0.5 cm is achieved. The loading cycle is repeated 3 times. Since there are no significant differences in the stress strain profiles of the repeat cycles, Young's Modulus $E_0$ are determined to be 208 kPa based on the mean of the 3 cycles.

In a first aspect, a method of making a bone matrix includes exposing a bone tissue to a solution including a surfactant and a protease, treating the bone tissue with an acid solution following exposing the bone tissue, and electrophoretically treating the acid treated bone tissue.

In an example, the protease includes subtilisin.

In an example of the first aspect and the above examples, the solution includes the protease in an amount in a range of 0.01 wt % to 1.0 wt %. For example, the range is 0.01 wt % to 0.5 wt % or the range is 0.01 wt % to 0.1 wt %.

In another example of the first aspect and the above examples, the surfactant includes an anionic surfactant. For example, the anionic surfactant includes sulfate surfactant. In an example, the sulfate surfactant includes dodecylbenzene sulfonic acid or a salt thereof.

In a further example of the first aspect and the above examples, the solution includes the surfactant in an amount in a range of 0.05 wt % to 5.0 wt %. For example, the range is 0.05 wt % to 1.5 wt %. In another example, the range is 0.05 wt % to 0.5 wt %.

In an additional example of the first aspect and the above examples, treating with the solution includes treating for between 10 hours and 48 hours. For example, treating with the solution includes treating for between 16 hours and 36 hours. In an example, treating with the solution includes treating for between 20 hours and 28 hours.

In another example of the first aspect and the above examples, the acid solution includes nitric acid, sulfuric acid, or hydrochloric acid. For example, the acid solution includes hydrochloric acid.

In a further example of the first aspect and the above examples, the acid solution includes acid in a concentration in a range of 0.1M to 3M. For example, the range is 0.3M to 2M or the range is 0.5M to 1.5M.

In an additional example of the first aspect and the above examples, treating with the acid solution includes treating for between 12 hours and 72 hours. For example, treating with the acid solution includes treating for between 20 hours and 56 hours or includes treating for between 32 hours and 50 hours.

In another example of the first aspect and the above examples, electrophoretically treating includes electrophoretically treating in a surfactant solution. For example, the surfactant solution includes 0.5 wt % to 5 wt % surfactant or includes 0.5 wt % to 2 wt % surfactant.

In a further example of the first aspect and the above examples, electrophoretically treating includes treating for 2 hours to 12 hours. For example, electrophoretically treating includes treating for 2 hours to 8 hours.

In an additional example of the first aspect and the above examples, electrophoretically treating includes treating at a potential of 20V to 80V. For example, electrophoretically treating includes treating at a potential of 32V to 64V or includes treating at a potential of 40V to 60V.

In another example of the first aspect and the above examples, electrophoretically treating includes treating at a power of 5 W to 30 W. For example, electrophoretically treating includes treating at a power of 10 W to 25 W or includes treating at a power of 12 W to 18 W.

In a further example of the first aspect and the above examples, electrophoretically treating includes treating at a current of 100 mA to 500 mA. For example, electrophoretically treating includes treating at a current of 200 mA to 400 mA or includes treating at a current of 250 mA to 350 mA.

In an additional example of the first aspect and the above examples, the method further includes washing the bone tissue with water after exposing and before treating with an acid solution.

In another example of the first aspect and the above examples, the method further includes washing the bone tissue with water after treating with an acid solution and before electrophoretically treating.

In a further example of the first aspect and the above examples, the method further includes electrophoretically treating the acid treated bone tissue in the presence of water after electrophoretically treating.

In a second aspect, a bone matrix has a DNA content of not greater than 0.1 micrograms per milligram sample and a modulus in a range of 150 kPa to 300 kPa.

In an example of the second aspect, the DNA content is in a range of 0.01 micrograms per milligram sample to 0.1 micrograms per milligram sample. For example, the DNA content is in a range of 0.01 micrograms per milligram sample to 0.05 micrograms per milligram sample or is in a range of 0.01 micrograms per milligram sample to 0.45 micrograms per milligram sample.

In another example of the second aspect and the above examples, the bone matrix further has an alpha-gal content in a range of 0.005 ng/ml to 0.5 ng/ml. For example, the alpha-gal content is in a range of 0.005 ng/ml to 0.3 ng/ml, is in a range of 0.01 ng/ml to 0.2 ng/ml, or is in a range of 0.01 ng/ml to 0.1 ng/ml.

In a further example of the second aspect and the above examples, the bone matrix retains 85% collagen I. For example, the bone matrix retains at least 88% collagen I, at least 90% collagen I, or at least 91% collagen I.

In an additional example of the second aspect and the above examples, the bone matrix has collagen I in an amount of 0.5 mg/g wet sample to 1.1 mg/g wet sample. For example, the bone matrix has collagen I in an amount of 0.7 mg/g wet sample to 1.0 mg/g wet sample or in an amount of 0.8 mg/g wet sample to 1.0 mg/g wet sample.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of making a bone matrix, the method comprising:
    exposing a bone tissue to a solution including a surfactant and a protease;
    treating the bone tissue with an acid solution following exposing the bone tissue; and
    electrophoretically treating the acid treated bone tissue.
2. The method of claim 1, wherein the protease includes subtilisin.
3. The method of claim 1, wherein the solution includes the protease in an amount in a range of 0.01 wt % to 1.0 wt %.
4. The method of claim 1, wherein the surfactant includes an anionic surfactant.
5. The method of claim 4, wherein the anionic surfactant includes sulfate surfactant.
6. The method of claim 5, wherein the sulfate surfactant includes dodecylbenzene sulfonic acid or a salt thereof.
7. The method of claim 1, wherein the solution includes the surfactant in an amount in a range of 0.05 wt % to 5.0 wt %.
8. The method of claim 1, wherein treating with the solution includes treating for between 10 hours and 48 hours.
9. The method of claim 1, wherein the acid solution includes nitric acid, sulfuric acid, or hydrochloric acid.
10. The method of claim 1, wherein the acid solution includes hydrochloric acid.
11. The method of claim 1, wherein the acid solution includes acid in a concentration in a range of 0.1M to 3M.
12. The method of claim 1, wherein treating with the acid solution includes treating for between 12 hours and 72 hours.
13. The method of claim 1, wherein electrophoretically treating includes electrophoretically treating in a surfactant solution.
14. The method of claim 13, wherein the surfactant solution includes 0.5 wt % to 5 wt % surfactant.
15. The method of claim 1, wherein electrophoretically treating includes treating for 2 hours to 12 hours.
16. The method of claim 1, wherein electrophoretically treating includes treating at a potential of 20V to 80V.
17. The method of claim 1, wherein electrophoretically treating includes treating at a power of 5 W to 30 W.
18. The method of claim 1, wherein electrophoretically treating includes treating at a current of 100 mA to 500 mA.
19. The method of claim 1, further comprising washing the bone tissue with water after treating with an acid solution and before electrophoretically treating.
20. The method of claim 1, further comprising electrophoretically treating the acid treated bone tissue in the presence of water after electrophoretically treating.

* * * * *